(12) United States Patent
Mizutani

(10) Patent No.: US 6,371,948 B1
(45) Date of Patent: Apr. 16, 2002

(54) SANITARY NAPKIN

(75) Inventor: Satoshi Mizutani, Kagawa-ken (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/302,767

(22) Filed: Apr. 30, 1999

(30) Foreign Application Priority Data

May 1, 1998 (JP) .......................................... 10-122498

(51) Int. Cl.[7] .............................................. A61F 13/15
(52) U.S. Cl. ............. 604/385.01; 604/378; 604/385.26; 604/329; 156/227
(58) Field of Search .................. 604/358, 500, 604/540, 358.23

(56) References Cited

U.S. PATENT DOCUMENTS

| | | | | |
|---|---|---|---|---|
| 4,701,177 A | * | 10/1987 | Ellis ....................... | 604/385.26 |
| 5,300,055 A | * | 4/1994 | Buell ...................... | 604/385.01 |
| 5,336,208 A | * | 8/1994 | Rosenbluth ................. | 604/329 |
| 5,558,656 A | * | 9/1996 | Bergman ................ | 604/385.01 |
| 5,591,150 A | * | 1/1997 | Olsen ..................... | 604/385.01 |
| 5,624,421 A | * | 4/1997 | Dabi ........................ | 604/378 |
| 5,653,842 A | * | 8/1997 | Kuen .......................... | 156/227 |
| 5,968,027 A | * | 10/1999 | Cole ..................... | 604/385.01 |
| 6,210,385 B1 | * | 4/2001 | Mizutani ............... | 604/385.01 |

FOREIGN PATENT DOCUMENTS

| | | | | |
|---|---|---|---|---|
| EP | 0768072 A1 | * | 4/1997 | ................. 604/358 |
| EP | 0 768 072 A1 | | 4/1997 | ................. 604/358 |
| EP | 0904755 A2 | * | 3/1999 | ................. 604/358 |
| EP | 0972502 A2 | * | 1/2000 | ................. 604/358 |
| EP | 0 972 502 A2 | | 1/2000 | ................. 604/358 |
| GB | 2319186 A | * | 5/1998 | ................. 604/358 |
| GB | 2 319 186 A | | 5/1998 | ................. 604/358 |
| JP | 6-502336 | | 3/1994 | |
| WO | WO 9416658 | * | 8/1994 | ................. 604/358 |
| WO | WO 94/16658 | | 8/1994 | ................. 604/358 |
| WO | WO 9531165 | * | 11/1995 | ................. 604/358 |
| WO | WO 95/31165 | | 11/1995 | ................. 604/358 |
| WO | WO 9707763 | * | 3/1997 | ................. 604/358 |
| WO | WO 97/07763 | | 3/1997 | ................. 604/358 |

* cited by examiner

Primary Examiner—John J. Calvert
Assistant Examiner—Angela J Grayson
(74) Attorney, Agent, or Firm—Baker & Daniels

(57) ABSTRACT

A sanitary napkin includes a liquid-pervious topsheet, a liquid-absorbent core, a shape-retaining panel lining the core and a back side member. The core and the shape-retaining panel are configured so as to present inverted V-shaped cross-sections, respectively, and attached to the back side member which is substantially flat. The napkin thus constructed allows at least the inverted V-shaped cross-sections to follow a movement of the wearer's body.

6 Claims, 1 Drawing Sheet

SANITARY NAPKIN

BACKGROUND OF THE INVENTION

The present invention relates to sanitary napkins or menstruation pads for absorption and containment of body exudates.

Japanese Patent Application (PCT) Disclosure Gazette No. Hei6-502336 discloses a sanitary napkin comprising a liquid-pervious topsheet, a liquid-impervious backsheet, a liquid-absorbent core and spacer means functioning to maintain the topsheet spaced from the core. The napkin of such arrangement is maintained at a predetermined position relative to a wearer's body even when an undergarment worn by the wearer of the napkin can not properly follow a movement of the weaver.

The spacer means of the above mentioned napkin is provided between the topsheet and the core and comprises tube or roll means through which body exudates should pass before absorbed by the core. Such manner of absorption is disadvantageous from the viewpoint of a rapidity and not suitable for the case in which a large amount of body exudates occurs at once.

SUMMARY OF THE INVENTION

In view of the problem as has been described above, it is an object of the present invention to provide a sanitary napkin improved so that the napkin can properly follow a movement of the wearer and rapidly absorb menstrual discharge.

According to the present invention, there is provided a sanitary napkin having a longitudinal direction and a transverse direction being orthogonal to the longitudinal direction, the napkin comprising a liquid-pervious topsheet, a back side member at least including a liquid-impervious sheet and a liquid-absorbent core disposed between the topsheet and the back side member, wherein:

the core presents, at a middle region of the longitudinal direction, an inverted V-shaped cross-section; the topsheet is placed upon an upper surface of the core while the core is lined by a shape-retaining panel having, in the transverse direction, a rigidity higher than that of the core and presenting an inverted V-shaped cross-section of a V-angle substantially identical to that of the core; the back side member extends outwards horizontally beyond transversely opposite side edges of the inverted V-shaped cross-section presented by the core; the topsheet is bonded to the upper surface of the back side member in regions thereof extending outwards beyond the side edges of the core; and the cross-section defines a substantially triangular space.

According to one embodiment of the invention, the back side member comprises a liquid-impervious plastic film.

According to another embodiment of the present invention, the back side member comprises a liquid-pervious sheet, a liquid-impervious sheet and a liquid-absorbent core disposed therebetween so that the liquid-pervious sheet and the liquid-impervious sheet define upper and lower surfaces of the back side member, respectively.

According to still another embodiment of the present invention, in the transverse direction of the napkin, the topsheet forms a pair of side flaps obliquely outwards and upwards extending beyond regions along which the topsheet is bonded to the back side member and the side flaps are provided in the vicinity of their ridges with elastic members extending in the longitudinal direction and bonded under tension to the respective side flaps so that the sanitary napkin presents a substantially W-shaped cross-section.

According to yet another embodiment of the present invention, the back side member is provided on its lower surface with adhesive fastener means used to fasten the napkin to an undergarment worn by the wearer of the napkin.

According to further additional embodiment of the present invention, the shape-retaining panel is made of a resilient material.

DETAILED DESCRIPTION OF THE PREFERRED EMBODIMENTS

Details of a sanitary napkin or menstruation pad exploited according to the present invention will be more fully understood from the description given hereunder with reference to the accompanying drawings.

Figure 1:
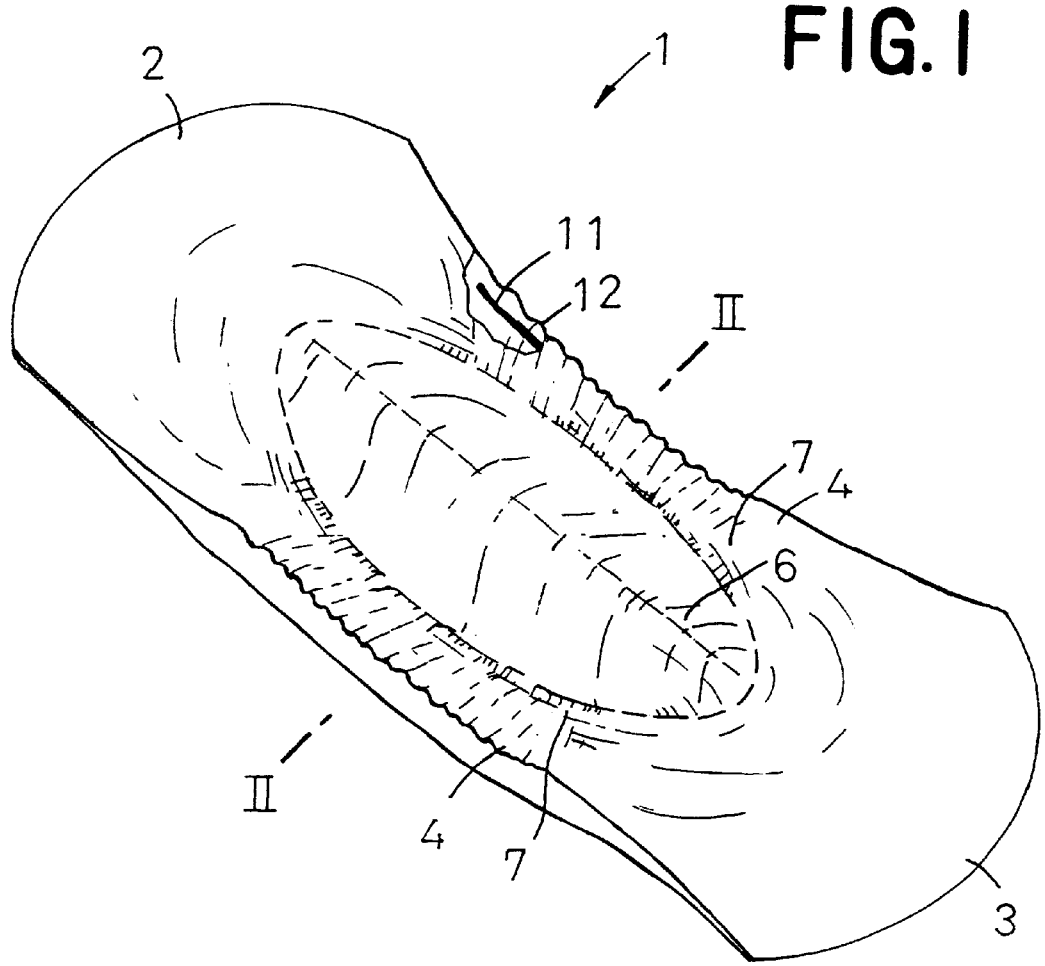
FIG. 1 is a perspective view showing a partly cut away sanitary napkin according to the present invention.

A sanitary napkin 1 shown by FIG. 1 in a partly cut away perspective view is elongate and defined by a front end 2, a rear end 3 and transversely opposite side edges 4. A transversely middle zone 6 and the side edges 4 of the napkin rise to form troughs 7 between the respective side edges 4 and the middle zone 6. The side edges 4 are respectively provided with first elastic members 11 extending longitudinally and secured thereto under appropriate tension so that a plurality of gathers 12 are formed along the respective side edges 4 as the first elastic members 11 contract.

Figure 2:
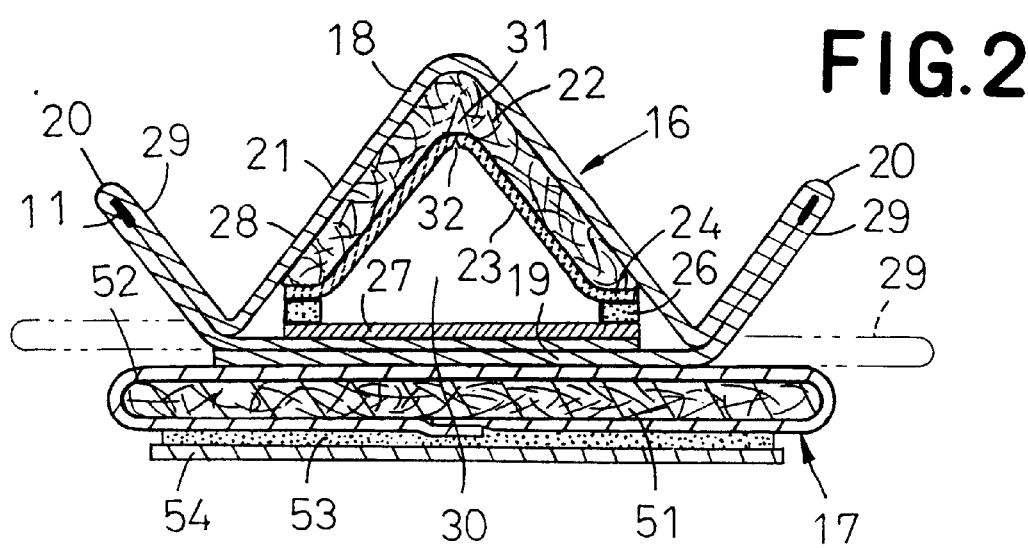
FIG. 2 is a sectional view taken along line II—II in FIG. 1.

FIG. 2 is a sectional view taken along line II—II in FIG. 1. The napkin 1 comprises an upper member 16 and a lower member 17. The upper member 16 comprises, in turn, a liquid-pervious topsheet 21, a liquid-absorbent core 22 and a shape-retaining panel 23. The liquid-pervious topsheet 21 has an upper portion curved to present a W-shaped cross-section and a flat bottom portion 19. The liquid-absorbent core 22 is laid in contact with a lower surface of the topsheet 21 in its upper portion 18 so as to present an inverted V-shaped cross-section. The shape-retaining panel 23 is laid in contact with a lower surface of the core 22 so as to prevent an inverted V-shaped cross-section. A second elastic member 27 is secured under appropriate tension to transversely opposite side edges 24 of the shape-retaining panel 23 by means of hot melt adhesive 26 and extends between the side edges 24 so that the shape-retaining panel 23 is maintained in the inverted V-shaped cross-section under contractile effect of the elastic member 27 while the panel 23 retains the inverted V-shaped cross-section of the core 22.

The topsheet 21 is intermittently bonded to an upper surface of the core 22 along its middle zone as viewed transversely of the napkin 1 so that the topsheet 21 may have a region 28 presenting an inverted V-shaped cross-section. Along the side edges 4 of the napkin 1, the topsheet 21 rises obliquely upwards to form a pair of side flaps 29. A ridge 20 of each flap 29 is formed by folding the topsheet 21 back onto itself and adhesively bonding the first elastic member 11 under appropriate tension between respective inner surfaces of these two layers of the folded topsheet 21. The topsheet 21 thus folded back further extends below the region 28 of the inverted V-shaped cross-section and forms the flat bottom portion 19. The bottom portion 19 comprises transversely opposite edge regions of the topsheet 21 placed upon and intermittently bonded to each other. A lower surface of the bottom portion 19 is intermittently bonded to an upper surface of the lower member 17.

The core 22 is formed by fluff pulp or a mixture of fluff pulp and super absorptive polymer particles, preferably covered with a tissue paper. The core 22 is formed at its transversely middle with a groove 31 extending longitudinally thereof so that the core 22 may be easily bent along the groove 31 in the inverted V-shape.

The shape-retaining panel 23 is made of a sheet material such as a nonwoven fabric, a plastic film or an apertured plastic film and preferably, a resilient sheet having, transversely of the napkin 1, a bending stiffness which is higher than that of the core 22. Such sheet material may be liquid-pervious or liquid-impervious and may be breathable or unbreathable. The shape-retaining panel 23 has its upper surface intermittently bonded to the lower surface of the core 22 and has its lower surfaces provided the second elastic member 27 bonded with under appropriate tension to the side edges 24 so that the second elastic member 27 may extend between the side edges 24. The shape-retaining panel 23 presents its inverted V-angle which is substantially identical to the inverted V-angle presented by the core 22. If desired, a lower surface of the panel 23 may also be provided at its transversely middle with a groove 32 extending longitudinally thereof so that the panel 23 can be easily bent in an inverted V-shaped cross-section along the groove 32. When the panel 23 comprises a suitable thermoformable sheet material such as a nonwoven fabric made of thermoplastic synthetic fibers molded in the inverted V-shaped cross-section, use of the second elastic member 27 may be eliminated.

The second elastic member 27 may be provided in a selective form, for example, in the form of a rubber sheet, an elastic nonwoven fabric, or an inelastic nonwoven fabric to which a plurality of rubber threads bonded under appropriate tension. The lower surface of the second elastic member 27 may be bonded or not bonded to the portion of the topsheet 21 intended to be in contact with the lower surface. A cavity 30 presenting a triangular cross-section is formed between the second elastic member 27 and the backsheet 23.

The side flaps 29 are adapted to be pressed against both sides of a wearer's vaginal orifice and thereby to prevent body exudates from leaking sideways. The side flaps 29 may be subjected to water repellent finish, if desired. The napkin 1 according to the illustrated embodiment is provided with the side flaps 29 and presents a W-shaped cross-section which facilitates the napkin 1 to be placed against the wearer's vaginal orifice and a zone therearound. It should be understood, however, that the present invention may be exploited as a napkin of which the side flaps 29 are substantially horizontal as indicated by imaginary lines or as a napkin provided with none of the side flaps 29.

The lower member 17 principally serves to fix the upper member 16 to an undergarment worn by the wearer of the napkin. The lower member 17 can be used also as the absorbent member and/or the liquid-impervious member to prevent the undergarment from being stained with body exudates. According to the illustrated embodiment, the lower member 17 comprises a core 51, a cover sheet 52 covering upper and lower surfaces of the core 51 and adhesive 53 applied on the lower surface of the sheet 52. The core 51 is provided in the form of preformed fluff pulp or preformed fluff pulp/thermoplastic synthetic fiber mixture, or made of the other material such as a nonwoven fabric, a urethane sponge sheet or a soft foamed sheet. The cover sheet 52 may be made of a nonwoven fabric, a plastic film, an apertured plastic film, etc. The cover sheet 52 may be formed by combination of a liquid-pervious sheet covering the upper surface of the core 51 and a liquid-impervious sheet covering the lower surface of the core 51. The core 51 may be intermittently bonded to the cover sheet 52 or not bonded to the cover sheet 52 at all. The adhesive 53 is protectively covered with a release paper 54. The lower member 17 may be formed by the liquid-impervious plastic film alone so far as the member 17 requires neither absorbability nor cushioning effect.

In actual use, the napkin 1 arranged as has been described above is fixed by the adhesive 53 to the undergarment worn by the wearer of the napkin, thereupon the transversely middle region having the inverted V-shaped cross-section is placed against the user's vaginal orifice and the region therearound and rapidly absorbs body exudates. At the same time, the side flaps 29 are placed against both sides of the vaginal orifice so as to prevent body exudates from leaking sideways. The presence of the shape-retaining panel 23, the elastic member 27 and the triangular cavity 30 enables the transversely middle zone having the inverted V-shaped cross-section to be relatively free to be elastically deformable vertically as well as horizontally as viewed in FIG. 2. Accordingly, even when a movement of the undergarment can not follow the movement of the user's body, particularly the vaginal orifice and the region therearound, the upper member 16 of the napkin 1 can properly follow the movement of the undergarment and thereby can reliably absorb body exudates. An excess of body exudates which has not been absorbed by the upper member 16 can be absorbed by the lower member 17. With this napkin 1, rapid absorption of body exudates is achieved by the unique arrangement that the core 22 is placed against the user's vaginal orifice with interposition of the topsheet 21.

To exploit the present invention, operation of bonding/joining respective members together may be achieved by utilizing suitable adhesive agent such as hot melt adhesive and, for the members which are of heat-sealable nature, the heat-sealing technique may be also useful for this purpose.

The sanitary napkin according to the present invention allows body exudates to be rapidly as well as reliably absorbed and, in addition, allows body exudates to be reliably prevented from leaking sideways even when the undergarment worn by the user can not follow the movement of the user's body. Specifically to describe, the liquid-absorbent core is configured so as to present an inverted V-shaped cross-section, i.e., to form a triangular cavity between the core and the lower member of the napkin so that not only the core may be reliably placed against the user's vaginal orifice and the region therearound but also free to follow the movement of vaginal orifice and the region therearound.

What is claimed is:

1. A sanitary napkin having a longitudinal direction and a transverse direction being orthogonal to said longitudinal direction, said sanitary napkin comprising:

a liquid-pervious topsheet;

a back side member which includes a liquid-impervious sheet;

a liquid-absorbent core disposed between said liquid-pervious topsheet and said back side member; and a shape-retaining panel in contact with a lower surface of the liquid-absorbent core, said liquid-absorbent core produces an inverted V-shaped cross-section at a middle region of said longitudinal direction, said liquid-pervious topsheet contacting an upper surface of said liquid-absorbent core, said shape-retaining panel has a rigidity which is higher than a rigidity of said liquid-absorbent core, and produces an inverted V-shaped cross-section which is substantially identical to that of the liquid-absorbent core, said back side member extending outward horizontally beyond transversely opposite side edges of said inverted V-shaped cross-section produced by said liquid-absorbent core, said topsheet being bonded to an upper surface of said back side member in regions thereof which extend outward beyond said opposite side edges of said liquid-absorbent core, so as to form a triangular space between sail liquid-absorbent core and said back side member, said back side member extending outward beyond opposite side edges of said regions at which said topsheet is bonded to the upper surface of said back side member.

2. A sanitary napkin according to claim 1, wherein said back side member comprises a liquid-impervious plastic film.

3. A sanitary napkin according to claim 1, wherein said back side member comprises:

a liquid-pervious sheet;

a liquid-impervious sheet; and a liquid-absorbent core disposed said liquid-pervious sheet and said liquid-impervious sheet so that said liquid-pervious sheet and said liquid-impervious sheet define upper and lower surfaces of said back side member, respectively.

4. A sanitary napkin according to claim 1, wherein, said topsheet forms a pair of side flaps which extend obliquely in said transverse direction and upwards beyond regions along which said topsheet is bonded to said back side member and said pair of side flaps include longitudinal ridges that are provided with elastic members extending in said longitudinal direction, said elastic members being secured under tension to the pair of side flaps so that said sanitary napkin presents a substantially W-shaped cross-section.

5. A sanitary napkin according to claim 1, wherein said back side member is provided on a lower surface with an adhesive material for fastening the sanitary napkin to an undergarment worn by wearer of the sanitary napkin.

6. A sanitary napkin according to claim 1, wherein said shape-retaining panel is made of a resilient material.

\* \* \* \* \*